United States Patent [19]

Mizutani

[11] Patent Number: 5,683,377
[45] Date of Patent: Nov. 4, 1997

[54] INDIVIDUALLY WRAPPED SANITARY NAPKIN

[75] Inventor: Satoshi Mizutani, Ehime-ken, Japan

[73] Assignee: Uni-Charm Corporation, Ehime-ken, Japan

[21] Appl. No.: 661,572

[22] Filed: Jun. 11, 1996

[30] Foreign Application Priority Data

Jun. 30, 1995 [JP] Japan .................. 7-165669

[51] Int. Cl.$^6$ .................. A61F 13/15; A61B 17/06
[52] U.S. Cl. .............. 604/390; 604/385.1; 604/387; 206/438
[58] Field of Search ............... 604/385.1, 386–390; 206/438–440

[56] References Cited

U.S. PATENT DOCUMENTS 5,413,568  5/1995  Roach et al. .

FOREIGN PATENT DOCUMENTS

| 5-9529 | 2/1993 | Japan . |
| 6-26833 | 4/1994 | Japan . |
| 6315504 | 11/1994 | Japan ............................ 604/389 |
| 2262235 | 6/1993 | United Kingdom . |
| 8810219 | 12/1988 | WIPO . |
| 9309743 | 5/1993 | WIPO . |
| 9409111 | 3/1994 | WIPO . |

Primary Examiner—John G. Weiss
Assistant Examiner—K. M. Reichle
Attorney, Agent, or Firm—Lowe, Price, LeBlanc & Becker

[57] ABSTRACT

An individually wrapped sanitary napkin in which a napkin includes a napkin body and a pair of wings extending from transversely opposite side edges of the napkin body. The napkin body is folded longitudinally thereof in a three layer overlapping relationship and the wings are also folded onto a top surface of the napkin body. Release sheets are releasably bonded onto adhesive zones provided on back surfaces of the napkin body and the wings, respectively. A wrapping sheet is also folded together with the napkin body so as to wrap the napkin body as well as the wings, wherein the respective release sheets are fixedly bonded to an inner surface of the wrapping sheet so that the wrapping sheet and the release sheet can be peeled off in the form of an integrated strip-like sheet from the napkin when removing the napkin from the wrapping sheet.

3 Claims, 4 Drawing Sheets

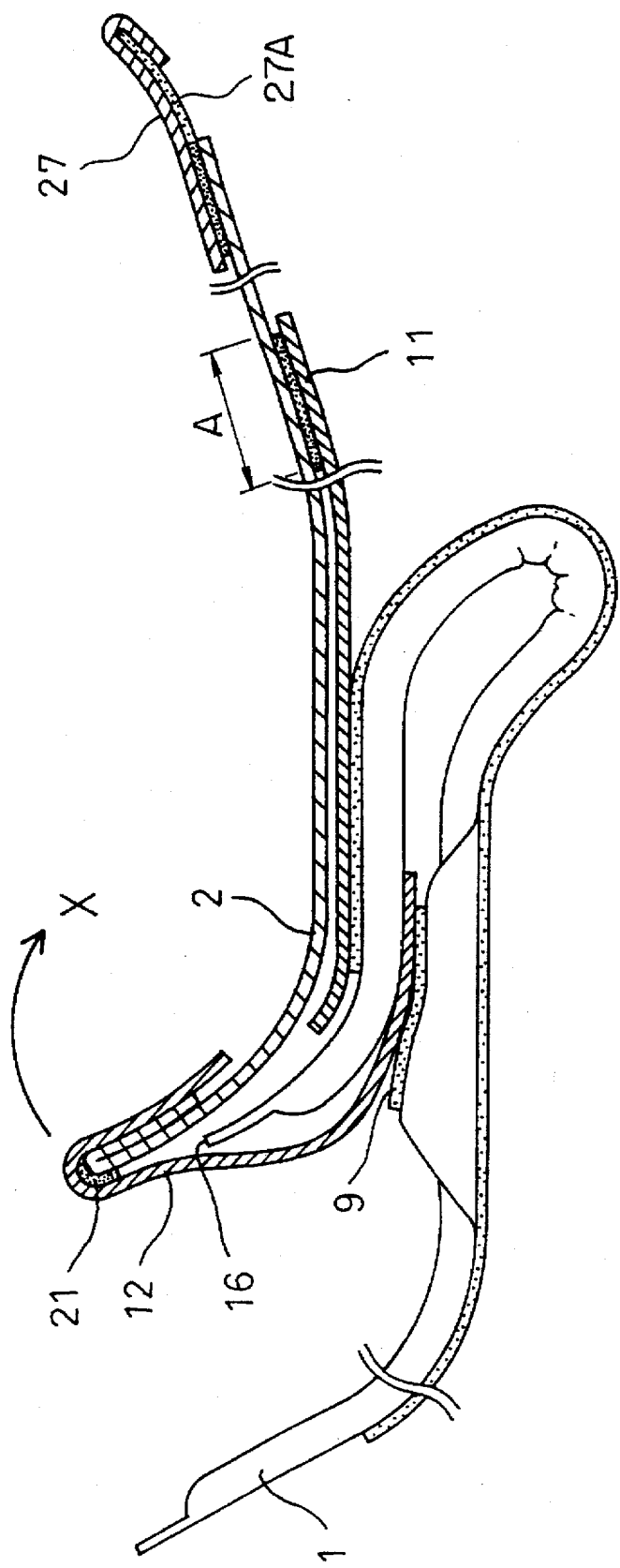

INDIVIDUALLY WRAPPED SANITARY NAPKIN

BACKGROUND OF THE INVENTION

The present invention relates to an individually wrapped sanitary napkin and, more particularly, a sanitary napkin or menstruation pad which is folded and individually wrapped by a wrapping sheet.

Sanitary napkins comprised at napkin body and a pair of wings, which are folded and individually wrapped, are known in the art. These napkin bodies and wings have adhesive applied thereto in selected areas and the adhesive is, covered with release sheets to prevent contamination with dust or the like. For example, Japanese Laid-Open Utility Model Application No. Hei6-26833 discloses an individually wrapped sanitary napkin in which adhesive zones on a napkin body are protectively covered with a first release sheet while adhesive zones on respective wings are protectively covered with a second release sheet. One end of the first release sheet longitudinally thereof is fixedly bonded to an inner surface of a napkin body wrapping sheet. Additionally, Japanese Laid-Open Utility Model Application No. Hei5-9529 discloses a sanitary napkin provided with a single substantially cross-shaped release sheet with protectively covers adhesive zones both on the body and wings of the sanitary napkin.

Disadvantageously the first and second release sheets must be separately peeled off requiring more time and effort in comparison with the case in which these two release sheets are peeled off at once with a single peeling stroke. According to the napkin disclosed in Japanese Laid-Open Utility Model Application No. Hei5-9529, on the other hand, a single release sheet is used and time and effort to peel it off is correspondingly less. However, the force of peeling the release sheet off tends to be decentralized on the marginal regions of the respective branches and the desired peeling cannot smoothly occur at these regions of the single release sheet. Accordingly, it is difficult to peel off this single release sheet as a whole at once.

It is a primary object of the invention to solve the problems of the prior art napkins as described above.

SUMMARY OF THE INVENTION

According to the invention, there is provided an individually wrapped sanitary napkin comprising a napkin including an elongate napkin body composed of a liquid-permeable topsheet, a liquid-impermeable backsheet and a liquid-absorbent core disposed therebetween, and having longitudinally opposite end edges and transversely opposite side edges, and a pair of wings extending outward beyond the transversely opposite side edges of the napkin body and having a top surface and a back surface.

A first release sheet is releasably bonded onto an adhesive zone provided on the backsheet.

A second release sheet is releasably bonded onto adhesive zones provided on the back surface of the wings which are folded onto the topsheet along the transversely opposite side edges of the napkin body.

An elongate long wrapping sheet is fixedly bonded to an outer surface of the first release sheet so that longitudinally opposite end edges and transversely opposite side edges of the wrapping sheet extend outward beyond the longitudinally opposite end edges and the transversely opposite side edges of the napkin body.

An assembly of the napkin and the wrapping sheet is folded with the topsheet lying inside and with a first longitudinal end of the napkin and the wrapping sheet underlying a second longitudinal end of the napkin and wrapping sheet. The transversely opposite side edges of the wrapping sheet are placed one upon another and sealed together. The wherein the longitudinal end edge of the wrapping sheet at the first longitudinal end edge of the napkin and wrapping sheet is directly fixedly bonded to the second release sheet.

With the individually wrapped sanitary napkin constructed as described above, one end of the wrapping sheet lying outside the folded napkin may be held between the wearer's fingers and pulled longitudinally of the napkin to peel the first release sheet releasably bonded to the napkin body off therefrom and then to peel the second release sheet releasably bonded to the wrapping sheet off from the wings.

BRIEF DESCRIPTION OF THE DRAWINGS

FIG. 4 is a schematic diagram of the sanitary napkin being removed from the wrapping sheet with a part of the wrapping sheet is omitted .

DESCRIPTION OF THE PREFERRED EMBODIMENT

Figure 1:
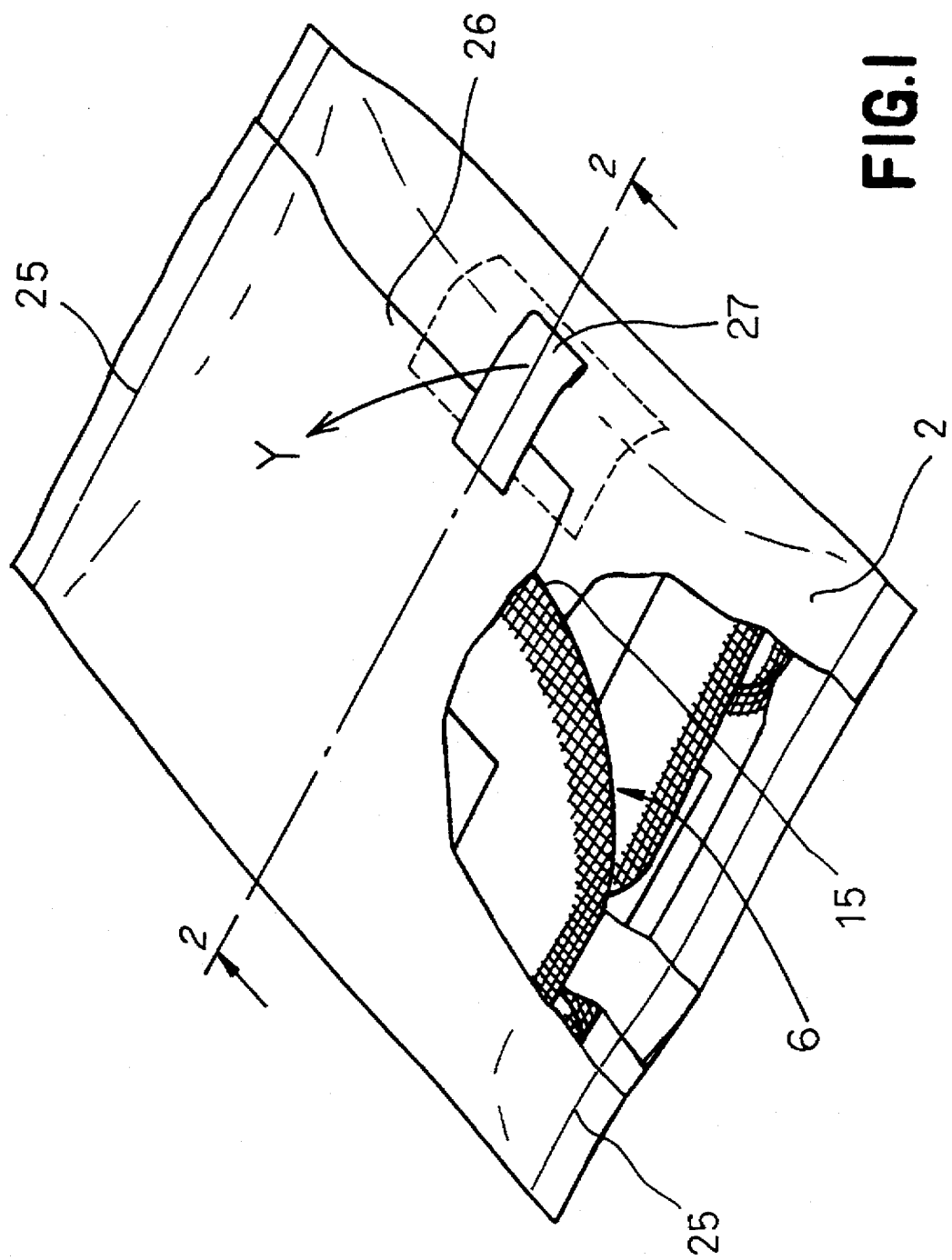
FIG. 1 is a partly cutaway perspective view of an individually wrapped sanitary napkin of the invention.
Figure 2:
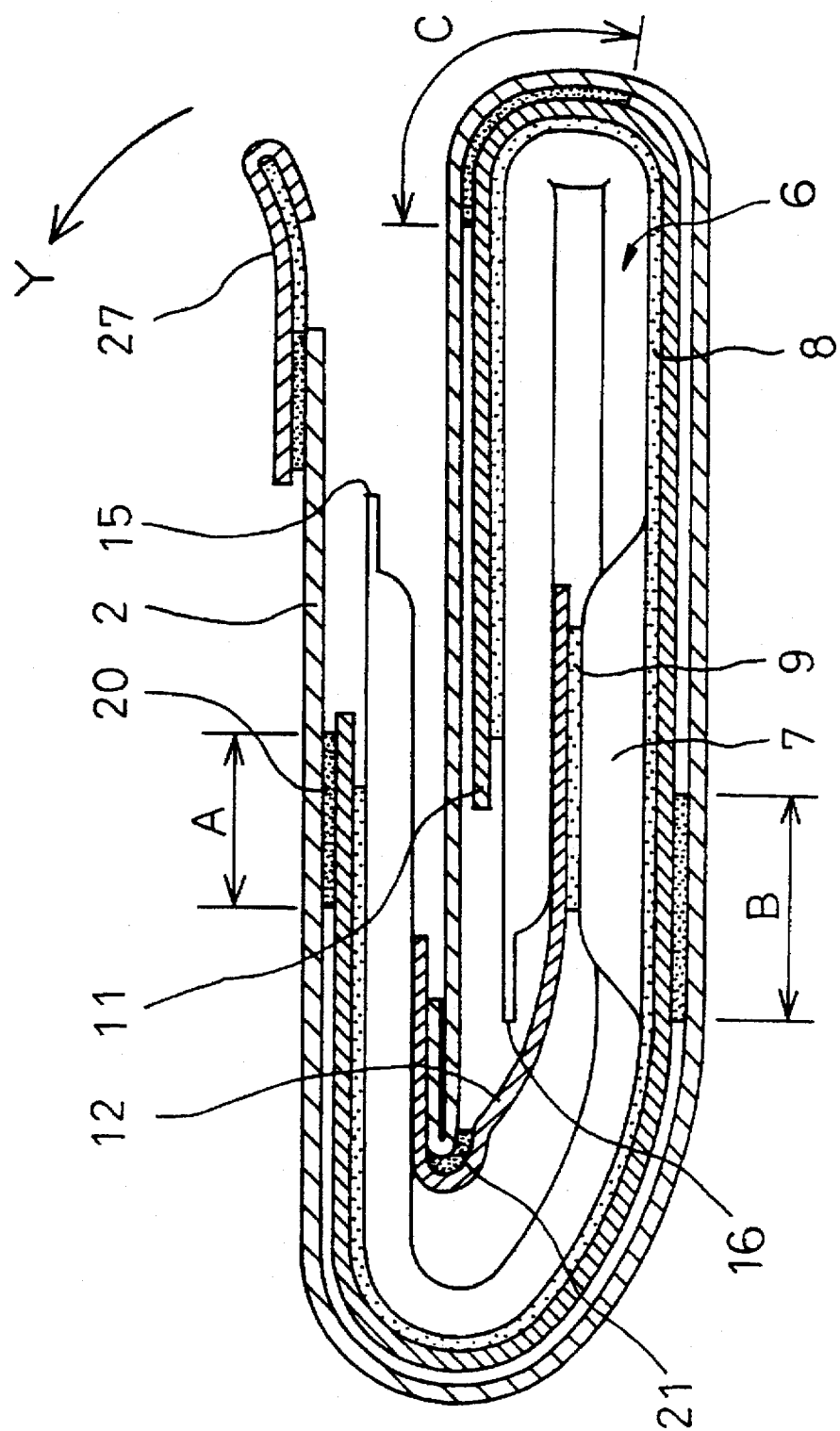
FIG. 2 is a sectional view taken along a line 2—2 in FIG. 1.
Figure 3:
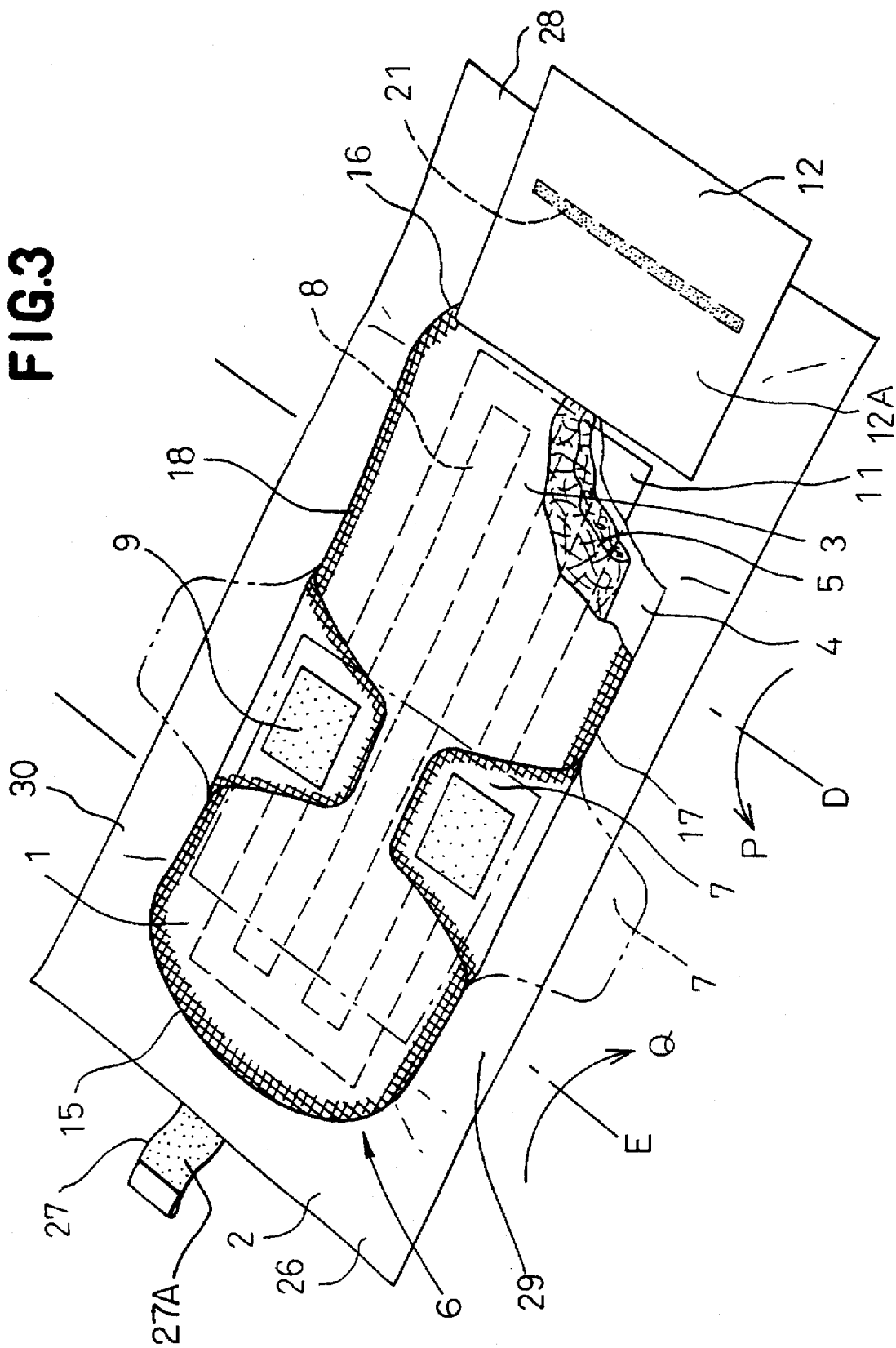
FIG. 3 is a perspective view of the individually wrapped sanitary napkin as longitudinally extended.

Referring to FIGS. 1 and 3, an individually wrapped sanitary napkin comprises a sanitary napkin or menstruation pad 1 and an elongate wrapping sheet 2. The napkin 1 comprises, in turn, an elongate napkin body 6 composed of a liquid-permeable topsheet 3, a liquid-impermeable backsheet 4 and a liquid-absorbent core 5 disposed between these two sheets 3, 4, and a pair of wings 7 formed by bonding together portions of the topsheet 3 and the backsheet 4. Wings 7 extend outward beyond transversely opposite side edges of the napkin body 6 (see FIG. 3). Surfaces of the napkin body 6 and the wings 7 are adjusted to be in contact with pants worn by a user as a result of a pair of first adhesive zones 8 and a pair of second adhesive zones 9, respectively. The first adhesive zones 8 extend in the longitudinal direction of the napkin body 6 and are releasably covered and protected with an elongate first release sheet 11. The second adhesive zones 9 are located on the respective wings 7 and are releasably covered and protected with a square or rectangle second release sheet 12, with wings 7 being folded along transversely opposite side edges 17, 18 of the napkin body 6, respectively, onto the topsheet 3. The wrapping sheet 2 has longitudinally opposite end edges 26, 28 and transversely opposite side edges 29, 30 extending outward beyond both the longitudinally opposite end edges 15, 16 and the transversely opposite side edges 17, 18 of the napkin body 6 (See FIG. 3) and fixedly bonded at desired regions, for example, regions A, B, C as indicated in FIG. 2, to an outer surface of the first release sheet 11 by means of hot melt adhesive 20. An assembly of the sanitary napkin 1 and the wrapping sheet 2 is now folded in a three laser overlapping relationship with the topsheet 3 lying inside and with the end edge 16 underlying the end edge 15 of the napkin body 6. The side edges 29, 30 of the wrapping sheet 2 are placed one upon another and bonded together along seal-lines 25 extending in the longitudinal direction of the wrapping sheet 2. The portion 26 of the wrapping sheet 2 extending outward beyond the end edge 15 of the napkin body 6 defines an opening of the individually wrapped sanitary napkin and a tab 27 extending outward beyond the end edge 26 is releasably bonded to an outer surface of the wrapping sheet 2 by means of adhesive 27A applied onto an inner surface of this tab 27. As shown by FIG. 2, the second release sheet 12 is fixedly bonded to the end edge 28 of the wrapping sheet 2 extending outward beyond the end edge 16 of the napkin body 6 by means of hot melt adhesive 21 and the second release sheet 12 covers the second adhesive zones 9.

Referring again to FIG. 3, the assembly of the sanitary napkin 1 and the wrapping sheet 2 is in an unfolded state. From this state, the assembly is folded in a three layer overlapping relationship, i.e., first along a folding line D in a direction indicated by an arrow P and then along a folding line E in a direction indicated by an arrow Q, with the end edge 16 underlying the end edge 15 of the napkin body 6. The state of the assembly thus folded corresponds to the state shown by FIGS. 1 and 2. In folding the assembly, an upper surface 12A, as viewed in FIG. 3, of the second release sheet 12 bonded to the wrapping sheet 2 is put against the second adhesive zones 9, then the tab 27 is releasably bonded to an outer surface of the wrapping sheet 2 and finally the seal-lines 25 are formed.

Referring again to FIG. 2 and referring also to FIG. 4, the wrapping sheet 2 is torn or peeled off and the first release sheet 11 also begins to be peeled off along the seal-lines 25 as the tab 27 is pulled in a direction indicated by an arrow Y. As the tab 27 is pulled, a pulling force is exerted also upon the second release sheet 12 and consequently the second release sheet 12 is pulled away from the second adhesive zones 9 in a direction indicated by an arrow X. The wrapping sheet 2 and the first and second release sheets 11, 12 can accordingly be smoothly peeled off the sanitary napkin in the form of an integrated strip-like sheet by a single stroke of this pulling operation. The integrated strip-like sheet may be easily crumpled into a wad and thrown away.

To make the individually wrapped sanitary napkin of the invention, the wrapping sheet 2 as well as the first and second release sheets 11, 12 may be made of materials conventionally employed for these components in the art, such as plastic films Bonding between the various elements of the napkin may be achieved by any suitable means such as hot melt adhesive, heat-welding or ultrasonic welding.

According to the invention, the first release sheet adapted to protect the adhesive zones provided on the napkin body is fixedly bonded to the wrapping sheet, and the second release sheet adapted to protect the adhesive zones provided on the wings is also fixedly bonded to the wrapping sheet. Accordingly, the invention allows the first and second release sheets to be smoothly peeled from the sanitary napkin merely by tearing the wrapping sheet and taking the napkin out therefrom, and in this operation, the first and second release sheets can not be peeled a from each other longitudinally of the napkin.

What is claimed is:

1. An individually wrapped sanitary napkin comprising:

a napkin including an elongate napkin body having a liquid-permeable topsheet, a liquid-impermeable backsheet and a liquid-absorbent core disposed and encased therebetween, said napkin body further having longitudinally opposite end edges and transversely opposite side edges, and a pair of wings extending outward beyond the transversely opposite side edges of said napkin body, each wing having a top surface and a back surface;

a first release sheet releasably bonded onto an adhesive zone provided on said backsheet;

a second release sheet releasably bonded onto adhesive zones provided on the back surface of said wings which are folded along the transversely opposite side edges of said napkin body onto said topsheet;

an elongate wrapping sheet being fixedly bonded to an outer surface of said first release sheet so that longitudinally opposite end edges and transversely opposite side edges of said wrapping sheet extend outward beyond the longitudinally opposite end edges and the transversely opposite side edges of said napkin body respectively, said napkin and said wrapping sheet being folded with said topsheet lying inside and with a first longitudinal end of said napkin and said wrapping sheet underlying a second longitudinal end of said napkin and wrapping sheet, the transversely opposite side edges of said wrapping sheet being placed one upon another and sealed together; and wherein the longitudinal end edge of said wrapping sheet at the first longitudinal end edge of said napkin and said wrapping sheet is directly and fixedly bonded to said second release sheet.

2. An individually wrapped sanitary napkin according to claim 1, further comprising a tab having an adhesive inner surface which extends outward beyond the longitudinal end edge of said wrapping sheet at the second longitudinal end edge of said napkin and wrapping sheet, said tab being fixedly bonded to said longitudinal end edge of said wrapping sheet at the second longitudinal end edge of said napkin and wrapping sheet, the adhesive inner surface of said tab being releaseably bonded onto an outer surface of a portion of said wrapping sheet to which said adhesive inner surface is opposed when the napkin and wrapping sheet are folded.

3. An individually wrapped sanitary napkin according to claim 1, wherein said wings are formed by bonding together portions of said topsheet and said backsheet which extend outward beyond the transversely opposite side edges of said napkin body.

\* \* \* \* \*